(12) United States Patent
Kubas

(10) Patent No.: US 11,034,217 B1
(45) Date of Patent: Jun. 15, 2021

(54) AUTOMOBILE AIR FRESHENER

(71) Applicant: Chandler Kubas, Dickinson, ND (US)

(72) Inventor: Chandler Kubas, Dickinson, ND (US)

( * ) Notice: Subject to any disclaimer, the term of this patent is extended or adjusted under 35 U.S.C. 154(b) by 207 days.

(21) Appl. No.: 16/227,969

(22) Filed: Dec. 20, 2018

Related U.S. Application Data

(60) Provisional application No. 62/608,343, filed on Dec. 20, 2017.

(51) Int. Cl.
| | | |
|---|---|---|
| *B60H 3/00* | (2006.01) | |
| *A61L 9/12* | (2006.01) | |
| *B60R 16/033* | (2006.01) | |

(52) U.S. Cl.
CPC .......... *B60H 3/0035* (2013.01); *A61L 9/122* (2013.01); *B60H 3/0028* (2013.01); *A61L 2209/133* (2013.01); *A61L 2209/16* (2013.01); *B60H 2003/0042* (2013.01); *B60R 16/033* (2013.01)

(58) Field of Classification Search
CPC .......... B60H 3/0035; B60H 2003/0042; B60R 16/033; A61L 9/122; A61L 2009/133; A61L 2009/16
USPC .......................................................... 454/143
See application file for complete search history.

(56) References Cited

U.S. PATENT DOCUMENTS

| | | |
|---|---|---|
| 4,968,456 A | 11/1990 | Muderlak et al. |
| 6,197,263 B1 | 3/2001 | Blount |
| 6,592,828 B2 | 7/2003 | Muñoz |
| 8,197,761 B1 | 6/2012 | Miller-Larry |
| D733,280 S | 6/2015 | Bourne |
| 2010/0065654 A1 | 3/2010 | Wheatley et al. |
| 2010/0187327 A1 | 7/2010 | Irvin |
| 2014/0112649 A1 | 4/2014 | Irvin et al. |

*Primary Examiner* — Steven B McAllister
*Assistant Examiner* — Allen R Schult
(74) *Attorney, Agent, or Firm* — Cramer Patent & Design, PLLC; Aaron R. Cramer

(57) ABSTRACT

An automobile air freshening system includes a housing with a forced air mechanism installed in-line within the cabin ventilation system of an automobile. The system is in electrical communication with the battery of the automobile and possess a dedicated fuse. The system is operated by a switch mounted within the dashboard of the automobile and switch located on the housing. There are multiple locations for the application of user-selected air freshener devices capable of being installed within the housing.

17 Claims, 2 Drawing Sheets

AUTOMOBILE AIR FRESHENER

RELATED APPLICATIONS

The present invention was first described in and claims the benefit of U.S. Provisional Application No. 62/608,343, filed Dec. 20, 2017, the entire disclosures of which are incorporated herein by reference.

FIELD OF THE INVENTION

The present invention relates generally to the field of an automobile air freshener.

BACKGROUND OF THE INVENTION

Given that many people use their motor vehicles on a daily basis, over time, the interior of the vehicle may develop unpleasant odors. These odors may be due to food that is consumed in the vehicle, engine emissions, perspiration from the motor vehicle driver and or occupants and soiled diapers of small children.

There are many devices available which purport to provide a solution to this problem but the most common usually involve an aerosol sprayed air freshener or a solid air freshener commonly hung from the rearview mirror. These fresheners are often either ineffective or so overpowering that they become worse than the problem they were intended to address. Additionally, the solid air fresheners may obstruct vision if hung from a mirror and are seldom aesthetically pleasing.

Accordingly, there exists a need for a means by which interior odors from motor vehicles can be neutralized using an air freshener by a means which is not readily apparent, yet functional. The development of the automobile air freshener fulfills this need

SUMMARY OF THE INVENTION

The principles of the present invention provide for an automobile air freshening system, comprising a housing having a hollow interior with an outlet port along a first side wall and a second side wall having a housing grate. The outlet port is located on the first side wall and is capable of having a fluid communication with a first end of tubing. The housing also has a fan and a blower motor which are secured within the housing. A first switch is disposed upon a front face of the housing and is in electrical communication between a fuse panel or a dedicated fuse. The front face of the housing includes a liquid air freshener port, a first air freshener housing door, and a second air freshener housing door. The battery of the automobile, the fuse panel or dedicated fuse is in electrical communication with the battery of the automobile and the blower motor. As a result, the first switch therefore controls power from the battery to the blower motor. The fan resides within the housing and is sited immediately adjacent to or in-line with the housing grate. The housing is mounted within the dashboard such that only the front face is accessible within the cabin to an operator of the automobile, immediately subjacent to the steering wheel.

The air freshening system also comprises a plumbed in-line with the cabin ventilation system that disperses into the cabin, a first switch which is disposed upon the housing, a second switch which is mounted on the dashboard adjacent a steering wheel of the automobile, one or more cartridges capable of emitting a scent are capable of insertion into the housing within a first air freshener cartridge housing and within a second air freshener cartridge housing, respectively and be fully concealed within and an air diffusion apparatus which is secured within a vent of the automobile. The air diffusion apparatus is in fluid communication with the outlet port of the housing by a length of tubing. The second end of the tubing is in fluid communication with the air diffusion apparatus. The second switch is secured within a second switch housing and is in electrical communication directly with the blower motor, such that activation of the second switch operates the fan.

The housing may be rectangular-shaped and may be secured within the glove box of the automobile or steering wheel. The blower motor may operably control the fan and is mounted to an inner surface of the housing. The blower motor may also be in electrical communication with the second switch. A liquid air freshener port may be located on the front face of the housing adjacent an upper wall. The liquid air freshener port may also be located on the upper wall while a liquid air freshener reservoir may be located immediately downstream, of the fan.

A fill tube is in fluid communication between the liquid air freshener port and the liquid air freshener reservoir. The liquid air freshener may be introduced to the liquid air freshener reservoir through the fill tube and fill a bottom of the liquid air freshener reservoir. The two side walls of the first air freshener cartridge housing include a first air freshener housing grate. The first air freshener housing grate may encompass all of the side walls of the first air freshener housing.

The second air freshener cartridge housing may comprise a box-like structure that is capable of securely retaining a second air freshener cartridge therein, either by a plurality of rails, a plurality of tracks, or a snug fit. An outer wall of the second air freshener cartridge housing may be a hinged second air freshener housing door with an opening means. The second air freshener housing door may be flush with the front face of the housing and is therefore accessible from the cabin of the automobile.

The second air freshener cartridge housing may be configured to fully align the second air freshener cartridge with the forced air flow induced by the fan when the automobile air freshening system is operating. To enable the emanating fragrance from the second air freshener cartridge to be transferred to the outlet port, the two side walls of the second air freshener cartridge housing have a second air freshener housing grate.

The second air freshener housing grate may encompass all of the side walls of the second air freshener housing. The second air freshener housing grate may also encompass a portion of the side walls of the second air freshener housing. The air freshening system may be in electrical communication with a battery of the automobile and possess a dedicated fuse.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

Figure 1:
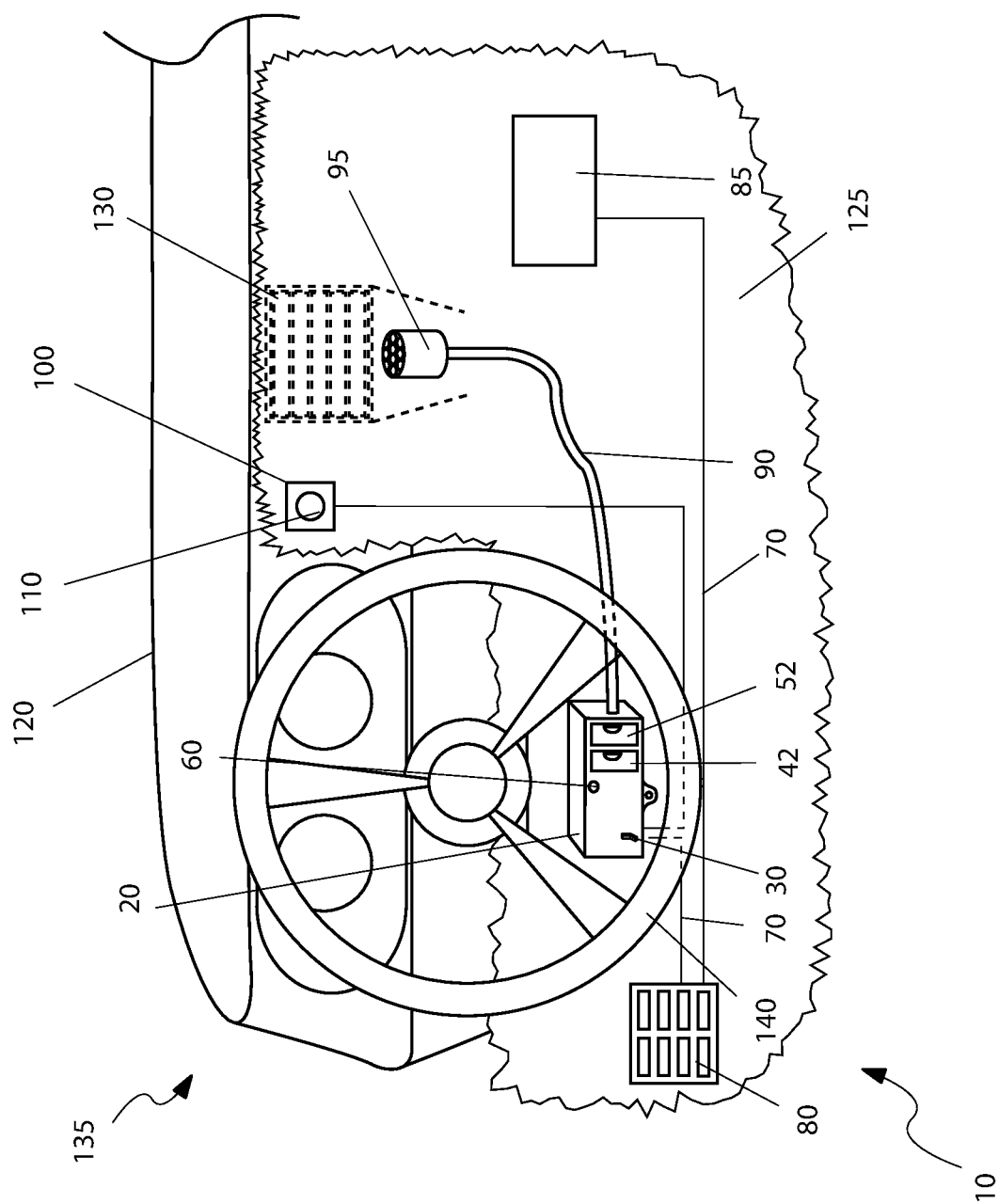
FIG. 1 is a perspective view of an automobile air freshening system 10, having a cut-away interior view of a dashboard 120 according to a preferred embodiment of the present invention; and, FIG. 2 is a close-up, partially cut-away view of the housing 20 with a blower motor 15 and fan 19, illustrating the features housed therewithin, according to a preferred embodiment of the present invention

DESCRIPTIVE KEY 10 automobile air freshening system
15 blower motor
19 fan
20 housing
21 housing grate
22 outlet port
30 first switch
39 first air freshener cartridge
40 first air freshener cartridge housing
41 first air freshener housing grate
42 first air freshener housing door
49 second air freshener cartridge
50 second air freshener cartridge housing
51 second air freshener housing grate
52 second air freshener housing door
59 liquid air freshener
60 liquid air freshener port
61 liquid air freshener fill tube
62 liquid air freshener reservoir
70 electrical wiring
80 fuse panel
85 battery
90 tubing
95 air freshener diffusion apparatus
100 second switch housing
110 second switch
120 dashboard
125 cabin
130 vent
135 automobile
140 steering wheel

DESCRIPTION OF THE INVENTION

The best mode for carrying out the invention is presented in terms of its preferred embodiment, herein depicted within FIG. 1. However, the invention is not limited to the described embodiment, and a person skilled in the art will appreciate that many other embodiments of the invention are possible without deviating from the basic concept of the invention and that any such work around will also fall under scope of this invention. It is envisioned that other styles and configurations of the present invention can be easily incorporated into the teachings of the present invention, and only one (1) particular configuration shall be shown and described for purposes of clarity and disclosure and not by way of limitation of scope.

The terms "a" and "an" herein do not denote a limitation of quantity, but rather denote the presence of at least one (1) of the referenced items.

The present invention describes an automobile air freshening system 10 (hereinafter the "system") comprising a housing 20 and a fan 19 with a motor 15 secured within the housing 20. The system 10 is installed within the dashboard 120 of a cabin 125 of an automobile 135 and plumbed in-line with the cabin ventilation system 130 that disperses into the cabin 125. The system 10 will be in electrical communication with the battery 85 of the automobile 135 and possess a dedicated fuse 80. The system 10 will be operated by a first switch 30 and a second switch 110. The first switch 30 will be disposed upon the housing 20 while the second switch 110 will be mounted on the dashboard 120 adjacent the steering wheel 140. Cartridges 39, 49 capable of emitting a scent are capable of insertion into the housing 20 within a first air freshener cartridge housing 40 and a second air freshener cartridge housing 50, respectively and be fully concealed within. Liquid air freshener 59 may also be added into the system 10 via the liquid air freshener port 60.

Referring now to FIG. 1, a perspective view of the system 10, according to a preferred embodiment of the present invention is disclosed. The system 10 generally comprises a rectangular housing 20 with a hollow interior with an outlet port 22 along a first side wall and a second side wall having a housing grate 21. The housing grate 21 can encompass the entire second side wall or a portion thereof. The outlet port 22 can be located at any position on the first side wall and is capable of having a fluid communication with a first end of tubing 90.

The first switch 30 is disposed upon a front face of the housing 20 and is in electrical communication between a fuse panel 80 or a dedicated fuse thereof, and the battery 85 of the automobile. The fuse panel 80 or dedicated fuse thereof is in electrical communication with the battery 85 of the automobile 135 and the blower motor 15. The first switch 30 therefore controls power from the battery 85 to the blower motor 15. The fan 19 is operably controlled by the blower motor 15. The fan 19 also resides within the housing 20 and is preferably sited immediately adjacent to or in-line with the housing grate 22. The housing 20 is mounted within the dashboard 120 such that only the front face is accessible within the cabin 125 to an operator of the automobile 135, preferably immediately subjacent to the steering wheel 140. Other mounting sites can be envisioned, such as in the glove box or to the side of the steering wheel 140 in orientations where other portions of the housing 20 are concealed or exposed. Other features present on the front face of the housing 20 is a liquid air freshener port 60, a first air freshener housing door 42, and a second air freshener housing door 52.

An air diffusion apparatus 95 is secured within a vent 130 of the automobile 135. The air diffusion apparatus 95 is in fluid communication with the outlet port 22 of the housing 20 by a length of tubing 90. The second end of the tubing 90 is in fluid communication with the air diffusion apparatus 95. The second switch 110 is secured within a second switch housing 100 and is in electrical communication directly with the blower motor 15. The fan 19 is operably controlled by the blower motor 15, such that activation of the second switch 110 operates the fan 19. In the preferred embodiment, the system 10 may be powered by activation of the first switch 30, thereby providing power to the fuse panel 80 or dedicated fuse from the on-board battery 25. Thereafter, provided the system 10 has at least one (1) air freshener cartridge 39, 49 or at least a quantity of liquid air freshener 59 disposed within the housing 20, upon activation of the second switch 110, the operator may disperse a fragrant aroma through the air freshener diffusion apparatus 95 and out the vent 130 to the cabin 125 of the automobile 135.

Figure 2:
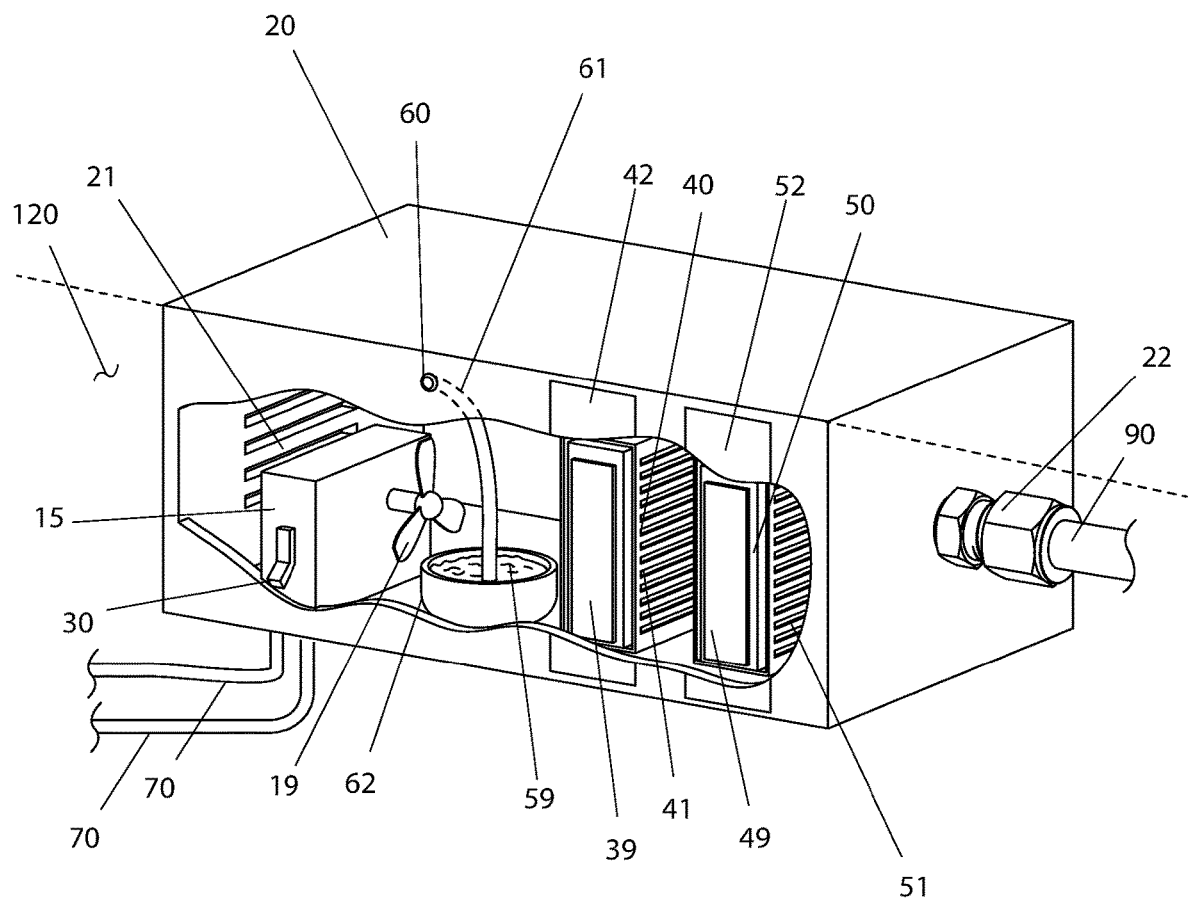

Referring more closely now to FIG. 2, the internal features of the housing 20 are illustrate and herein described. As aforementioned, the blower motor 15 and fan 19 reside within the housing 20, such that the fan 19 is adjacent to or in-line with the housing grate 22. The blower motor 19 operably controls the fan 19 and is mounted to an inner surface of the housing 20. The blower motor 15 is in electrical communication with the second switch 110. Located also on the front face of the housing 20, adjacent an upper wall, is a liquid air freshener port 60. In other embodiments, the liquid air freshener port 60 can be located on the upper wall. A liquid air freshener reservoir 62 is located immediately downstream, of the fan 19 and in-line therewith. A fill tube 61 is in fluid communication between the liquid air freshener port 60 and the liquid air freshener reservoir 62. Liquid air freshener 59 can be introduced to the liquid air freshener reservoir 62 through the fill tube 61 and fill the bottom of the liquid air freshener reservoir 62. The reservoir 62 is partially open such that the fan 19, when operated, can transfer the emanating fragrance from the liquid air freshener 59 downstream to the outlet port 22. Other embodiments may comprise a grate, a wicking membrane, or another feature than permits the fragrance to emit but restricts spillage for the top of the liquid air freshener reservoir 62.

Immediately downstream from the liquid air freshener reservoir 62 is a first air freshener cartridge housing 40. The first air freshener cartridge housing 40 is preferably a box-like structure that is capable of securely retaining a first air freshener cartridge 39 therein, either by rails, tracks, or merely a snug fit. The outer wall of the first air freshener cartridge housing 40 is a hinged first air freshener housing door 42 with an opening means. The first air freshener housing door 42 is flush with the front face of the housing 20 and is therefore accessible from the cabin 125 of the automobile 135. The first air freshener cartridge housing 40 is configured to fully align the first air freshener cartridge 39 with the forced air flow induced by the fan 19 when the system 10 is operating. To enable the emanating fragrance from the first air freshener cartridge 39 to be transferred to the outlet port 22, the two (2) side walls of the first air freshener cartridge housing 40 comprise a first air freshener housing grate 41. The first air freshener housing grate 41 may encompass all or a portion of the side walls of the first air freshener housing 40.

Immediately downstream from the first air freshener cartridge housing 40, and located adjacent to the outlet port 22, is a second air freshener cartridge housing 50. The second air freshener cartridge housing 50 is preferably a box-like structure that is capable of securely retaining a second air freshener cartridge 49 therein, either by rails, tracks, or merely a snug fit. The outer wall of the second air freshener cartridge housing 50 is a hinged second air freshener housing door 52 with an opening means. The second air freshener housing door 52 is flush with the front face of the housing 20 and is therefore accessible from the cabin 125 of the automobile 135. The second air freshener cartridge housing 50 is configured to fully align the second air freshener cartridge 49 with the forced air flow induced by the fan 19 when the system 10 is operating. To enable the emanating fragrance from the second air freshener cartridge 49 to be transferred to the outlet port 22, the two (2) side walls of the second air freshener cartridge housing 50 comprise a second air freshener housing grate 51. The second air freshener housing grate 51 may encompass all or a portion of the side walls of the second air freshener housing 50.

The system 10 may not be limited to one (1) air freshener diffusion apparatus 95 but rather utilize multiple diffusers 95 located in multiple vents 130. The system can be utilized with any combination of liquid air freshener 59, first air freshener cartridge 39, and second air freshener cartridge 49. Furthermore, any scent for the fragrance to be distributed is contemplated and should in no manner be limited by the disclosure herein. Lastly, the location of the system 10 may be secured at any location within the dashboard 120 due to preferences of the manufacturer, aftermarket installer, or operator of the automobile 135. It is also envisioned that certain embodiments of the invention can forgo the fuse panel 80 and the second switch 110, such that the system 10 can be powered by the first switch 30.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

The invention claimed is:

1. An automobile air freshening system, comprising:
a housing having a hollow interior with an outlet port along a first side wall and a second side wall having a housing grate, said outlet port is located on said first side wall and is capable of having a fluid communication with a first end of a tubing, said housing having a fan and a blower motor secured within said housing, a first switch is disposed upon a front face of said housing, said front face of said housing also includes a liquid air freshener port, a first air freshener housing door, and a second air freshener housing door, said fuse panel or dedicated fuse is in electrical communication with a battery of an automobile and said blower motor, said first switch therefore controls power from said battery to said blower motor, said fan resides within said housing and is immediately adjacent to or in-line with said housing grate, said housing is mounted within a dashboard such that only said front face is accessible within a cabin to an operator of said automobile, immediately subjacent to a steering wheel;
a plumbed in-line that disperses air into said cabin;
a second switch mounted on said dashboard adjacent said steering wheel of said automobile;
one or more cartridges capable of emitting a scent are capable of insertion into said housing within a first air freshener cartridge housing and within a second air freshener cartridge housing, respectively and be fully concealed within; and
an air freshener diffuser is secured within a vent of said automobile, said air freshener diffuser is in fluid communication with said outlet port of said housing by a length of said tubing, a second end of said length of tubing is in fluid communication with said air freshener diffuser, said second switch is secured within a second switch housing and is in electrical communication directly with said blower motor, such that activation of said second switch operates said fan.

2. The automobile air freshening system according to claim 1, wherein said housing is rectangular-shaped.

3. The automobile air freshening system according to claim 1, wherein said automobile includes a glove box.

4. The automobile air freshening system according to claim 1, wherein said blower motor operably controls said fan and is mounted to an inner surface of said housing.

5. The automobile air freshening system according to claim 1, wherein said liquid air freshener port located on said front face of said housing adjacent an upper wall.

6. The automobile air freshening system according to claim 5, wherein said liquid air freshener port is adjacent said upper wall and a liquid air freshener reservoir is located immediately downstream of said fan and in-line therewith.

7. The automobile air freshening system according to claim 6, further comprising a fill tube in fluid communication between said liquid air freshener port and said liquid air freshener reservoir.

8. The automobile air freshening system according to claim 7, wherein a liquid air freshener is introduced to said liquid air freshener reservoir through said fill tube and fills a bottom of said liquid air freshener reservoir.

9. The automobile air freshening system according to claim 1, wherein two side walls of said first air freshener cartridge housing includes a first air freshener housing grate.

10. The automobile air freshening system according to claim 1, wherein said second air freshener cartridge housing is a box-like structure that is capable of securely retaining a second air freshener cartridge of the one or more cartridges therein, either by a plurality of rails, a plurality of tracks, or held in place via friction with the housing.

11. The automobile air freshening system according to claim 10, wherein an outer wall of said second air freshener cartridge housing is the second air freshener housing door, wherein the second air freshener housing door is hinged.

12. The automobile air freshening system according to claim 1, wherein said second air freshener housing door is flush with said front face of said housing and is therefore accessible from said cabin of said automobile.

13. The automobile air freshening system according to claim 1, wherein said second air freshener cartridge housing is configured to fully align a second air freshener cartridge of the one or more cartridges with a forced air flow induced by said fan when said automobile air freshening system is operating.

14. The automobile air freshening system according to claim 13, wherein to enable an emanating fragrance from said second air freshener cartridge of the one or more cartridge to be transferred to said outlet port, two side walls of said second air freshener cartridge housing have a second air freshener housing grate.

15. The automobile air freshening system according to claim 14, wherein said second air freshener housing grate encompasses all side walls of said second air freshener housing.

16. The automobile air freshening system according to claim 14, wherein said second air freshener housing grate encompass a portion of side walls of said second air freshener housing.

17. The automobile air freshening system according to claim 1, wherein said battery of said automobile possesses a dedicated fuse.

* * * * *